(12) United States Patent
Klemola et al.

(10) Patent No.: US 7,775,713 B2
(45) Date of Patent: Aug. 17, 2010

(54) ARRANGEMENT FOR DENTAL IMAGING

(75) Inventors: Timo Klemola, Kerava (FI); Mika Anttila, Espoo (FI); Markku Nieminen, Vantaa (FI)

(73) Assignee: PaloDEx Group Oy (FI)

( * ) Notice: Subject to any disclaimer, the term of this patent is extended or adjusted under 35 U.S.C. 154(b) by 0 days.

(21) Appl. No.: 11/130,396

(22) Filed: May 16, 2005

(65) Prior Publication Data
US 2006/0257816 A1 Nov. 16, 2006

(51) Int. Cl.
A61C 3/00 (2006.01)
A61B 6/14 (2006.01)

(52) U.S. Cl. .......................... 378/191; 378/168; 433/29
(58) Field of Classification Search ................. 433/29, 433/24; 378/38, 39, 40, 168, 191
See application file for complete search history.

(56) References Cited

U.S. PATENT DOCUMENTS

| | | | |
|---|---|---|---|
| 5,113,424 A | 5/1992 | Burdea et al. | |
| 5,454,022 A | 9/1995 | Lee et al. | |
| 5,463,669 A | 10/1995 | Kaplan | |
| 5,503,320 A * | 4/1996 | Webster et al. | 227/176.1 |
| 5,510,623 A * | 4/1996 | Sayag et al. | 250/370.11 |
| 5,572,566 A | 11/1996 | Suzuki et al. | |
| 5,661,519 A * | 8/1997 | Franetzki | 348/66 |
| 5,828,721 A | 10/1998 | Schulze-Ganzlin et al. | |
| 6,042,267 A | 3/2000 | Muraki et al. | |
| 6,097,423 A * | 8/2000 | Mattsson-Boze et al. | 348/65 |
| 6,122,538 A * | 9/2000 | Sliwa et al. | 600/407 |
| 6,652,141 B1 * | 11/2003 | Cianciosi | 378/191 |
| 6,750,971 B2 * | 6/2004 | Overbeck et al. | 356/405 |
| 6,958,766 B2 * | 10/2005 | Cooper | 348/66 |
| 7,140,769 B2 * | 11/2006 | Kay | 378/168 |
| 7,311,440 B2 * | 12/2007 | Yoon et al. | 378/207 |
| 2002/0015934 A1 * | 2/2002 | Rubbert et al. | 433/29 |
| 2003/0026387 A1 | 2/2003 | Makila et al. | |
| 2003/0194056 A1 * | 10/2003 | Spahn | 378/205 |
| 2004/0218792 A1 * | 11/2004 | Spoonhower et al. | 382/128 |

FOREIGN PATENT DOCUMENTS

JP 10-282243 A 10/1998
WO WO-2006/008339 1/2006

OTHER PUBLICATIONS

French Search Report for corresponding French Patent Application No. 0604055, dated Jun. 14, 2009.

* cited by examiner

*Primary Examiner*—Cris L Rodriguez
*Assistant Examiner*—Heidi M Eide
(74) *Attorney, Agent, or Firm*—Andrus, Sceales, Starke & Sawall, LLP

(57) ABSTRACT

An arrangement for dental imaging having an intraoral sensor, which receives radiation at the moment of exposure for providing image data. The intraoral sensor comprises a housing (1), which encloses a detector and electronics and an orientation sensor (5), which senses orientation of the intraoral sensor at the moment of imaging to provide orientation information. A display unit (6, 7) and data transfer elements (3, 4), are connected to the detector and electronics for transmitting the image data and orientation information to the display unit. The display unit has image processing software, which processes the image data and utilizes the orientation information relevant to the image data for having an image to be presented on a display unit shown the right way.

4 Claims, 1 Drawing Sheet

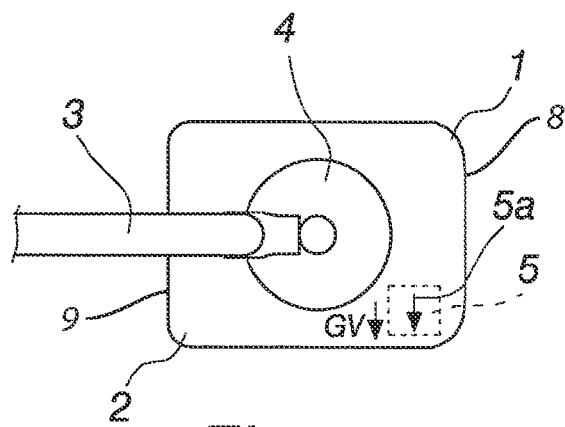
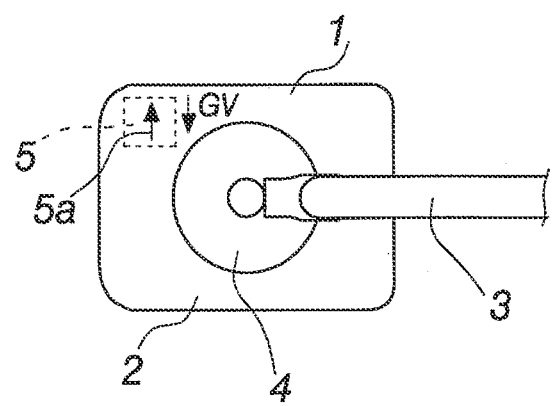
Fig. 1a (right)   Fig. 1b (left)
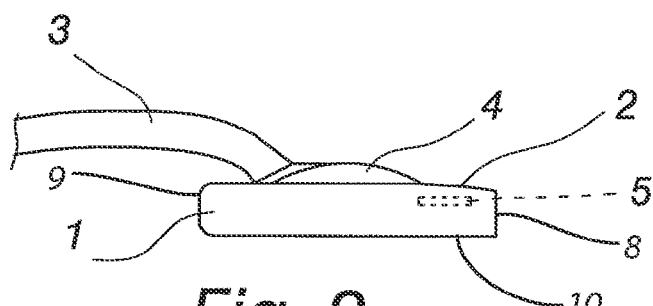
Fig. 2
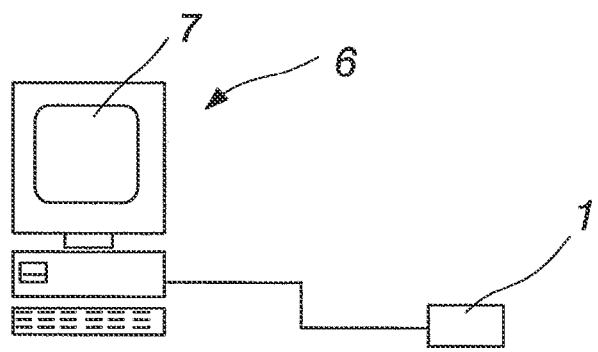
Fig. 3

ARRANGEMENT FOR DENTAL IMAGING

BACKGROUND AND SUMMARY

The invention relates to relates to an arrangement for dental imaging having an intraoral sensor, which receives radiation at the moment of exposure for providing image data.

In digital intraoral imaging, different positioning of a sensor is required depending on the imaging area and/or clinical needs (i.e. molar, premolar, bitewing images, etc.). Currently, the exposed image is rotated to the right orientation in the image processing software or the viewing software. The software has a feature where the user can select the orientation through the user interface before exposing the image. The prior art embodiments require user intervention to get the image rotated into the right orientation.

It is an objective of the present invention to provide an arrangement for dental imaging having intraoral sensor, which makes it possible to automatically display the image always in the right orientation. According to this invention, an intraoral sensor is provided, which receives radiation at the moment of exposure for providing image data, said intraoral sensor comprising a housing, which encloses a detector and electronics,
an orientation position sensor, which senses orientation of the intraoral sensor at the moment of exposure to provide orientation information,
said arrangement for dental imaging further comprising
a display unit for displaying image data and data transfer elements, which are connected to the detector and electronics for transmitting the image data and orientation information to the display unit, and
said display unit having coupled therewith image processing software, which processes the image data and utilizes the orientation information relevant to the image data for having an image to be presented on a display unit shown the right way.

In one of the preferred embodiments of the invention, the image processing software includes a pattern recognition algorithm, which enables pinpointing a tooth in question, based on the orientation information supplied by the orientation sensor and sensor location information determined on the basis of that.

The orientation sensor used in an intraoral sensor of the invention can be a small-size gravity sensor, such as e.g. a VTI Technologies SCA 1000 series accelerometer and/or a compass circuit, such as e.g. a Philips Semiconductors KMZ41 circuit, which both can be placed in a sensor housing. These sensors are micromachined (MEMS) components which are handled the same way as CMOS/CCD chips. Installation of an orientation sensor in the intraoral sensor is a reasonably straightforward procedure.

The inventive solution enables the use of angle information for correcting perspective errors of the image by making use of orientation information regarding the orientation sensor and possibly the tube head.

Among others, the invention provides benefits as follows:
a) The invention provides automated image adjustment.
b) By virtue of the invention, a certain message is obtained about which side of the mouth is being exposed to obtain an image. This is achieved because the intraoral sensor has to be placed to the mouth the right way up and the orientation sensor provides information, e.g. gravitational vector information, which makes sure which side of the mouth the is being exposed to obtain an image. This is because, if on the right side of the mouth the gravitational vector points to the same direction as the orientation sensor then on the left side of the mouth the gravitational vector has to point to an opposite direction with respect to the orientation sensor.
c) By obtaining a certain message about which side of the mouth has been exposed to obtain the image, and by also using pattern recognition, certain knowledge is provided about which tooth is depicted in each image, thus essentially eliminating possible misinterpretations.

BRIEF DESCRIPTION OF THE DRAWING

FIG. 1a is a schematic rear view of an intraoral sensor, which is fitted with an orientation sensor in accordance with the invention, in a position for placing it to the right side of the mouth, FIG. 1b is similar view than FIG. 1a but rotated 180° for placing it to the left side of the mouth, FIG. 2 shows the intraoral sensor of FIG. 1a in a side view, and FIG. 3 is a schematic view of the intraoral sensor connected to an image processing unit.

DETAILED DESCRIPTION

The intraoral sensor comprises a housing 1, which accommodates an image detector and necessary electronics. The housing 1 includes a leading edge 8, a trailing edge 9, a front surface 10 and a rear surface 2. The sensor has its rear surface 2 provided with a terminal element 4 for a communication cable 3 or other means for transmitting image data and position information to an image processing unit, designed e.g. as a computer 6, the image obtained as a result of an imaging procedure being displayed on its monitor 7. Alternatively it is possible to use wireless data transferring in transmitting image data and position information between intraoral sensor and image processing unit as for example described in US patent application US20030026387.

In the sensor housing 1 is placed an orientation sensor, which is depicted schematically by a dash-and-dot line 5 and which indicates the intraoral sensor's orientation depicted by an arrow 5a with respect to a gravitational vector GV or with respect to a magnetic field and its vectors.

The intraoral sensor 1 has to be placed to the mouth the right way such that its front surface is facing teeth. Therefore, the sensor 1 has to be rotated 180° when changing its position from one side to the other side. FIG. 1a shows the intraoral sensor 1 in a position for placing it to the right side of the mouth, in which case the gravitational vector GV points to the same direction as orientation sensor 5. FIG. 1b shows the intraoral sensor 1 in a position for placing it to the left side of the mouth, in which case the gravitational vector GV points to the opposite direction as orientation sensor 5.

The image processing software is preferably fitted with a pattern recognition algorithm, whereby, when the root portion of an imaged tooth points in a direction other than the direction of earth gravity given by the orientation sensor, the algorithm recognizes that the question is about upper teeth. Respectively, if the root of a tooth points in the direction of earth gravity, the question is about a lower tooth. Knowledge is always obtained from the image data itself, regarding about on which side of the mouth, the image is exposed, whereby, on the basis of orientation information supplied by the orientation sensor and position information received from the image data, the image can be depicted automatically the right way on a display monitor. This obviates the risk of misinterpretations.

The inventive solution allows for taking images more freely than before as the machine need not be informed at every image about where it has been exposed. In currently employed systems, a certain imaging sequence is applied in view of placing the images in a correct spot on a template to be displayed on a monitor screen.

Orientation information can also be utilized for focusing radiation to the intraoral sensor's detector to be assured that the correct side will be exposed. This can be done, e.g. by transmitting information of which side of the mouth is to be exposed from the orientation sensor to the X-ray source, where it can be made visible for the user, e.g. by using LEDs forming characters L (left) and R (right). The user can then position the X-ray source correctly for exposure. The information received from the orientation sensor can also be transmitted directly to a control device of the X-ray source for positioning the X-ray source automatically correctly for exposure.

It is recognized that various modifications and alterations may be made to the invention described above and it is intended to include within the present invention all such modifications and alterations as come within the scope of the following claims.

What is claimed is:

1. An arrangement for use with an X-ray source applying radiation at a moment of imaging to a dental structure in a mouth of a patient, the arrangement comprising:

a housing having a detector configured to detect radiation at the moment of imaging and to provide intraoral X-ray image data based on the detected radiation, the housing configured for positioning in the mouth of the patient in at least two complementary imaging positions, in one of which imaging positions the housing is inverted with respect to its orientation in the other imaging position;

an orientation sensor coupled to the housing and configured to sense orientation of the housing at the moment of imaging;

the orientation sensor further configured to identify which imaging position the housing is in at the moment of imaging by comparing the sensed orientation of the housing at the moment of imaging to a gravitational vector;

a display unit; and a communication link between the detector and orientation sensor and the display unit, the communication link configured to allow communication of the intraoral X-ray image data and the identified imaging position to the display unit;

wherein the display unit comprises a display and a controller that is configured to display an X-ray image on the display in a proper orientation by processing the intraoral X-ray image data and the identified imaging position;

wherein the controller is configured to identify features of the dental structure of the patient and display the X-ray image on the display in a proper orientation by processing the intraoral X-ray image data, identified imaging position, and identified features of the dental structure of the patient;

wherein the features of the dental structure of the patient comprise a root portion of an imaged tooth and wherein the controller is configured to compare the root portion to the gravitational vector to determine whether the intraoral X-ray image data relates to an upper or lower tooth in the mouth of the patient.

2. A method for applying radiation from an X-ray source to a dental structure in a mouth of a patient and providing an X-ray image of the dental structure in a correct orientation, the method comprising the steps of:

positioning an intraoral sensor into the mouth of the patient in one of two complementary imaging positions, in one of which imaging positions the intraoral sensor is inverted with respect to its orientation in the other imaging position;

applying radiation at a moment of imaging to the dental structure of the patient;

detecting radiation at the moment of imaging with the intraoral sensor;

providing image data based on the detected radiation;

sensing the orientation of the intraoral sensor at the moment of imaging;

detecting which imaging position the intraoral sensor is in at the moment of imaging by comparing the sensed orientation of the intraoral sensor to a gravitational vector;

communicating the image data and detected imaging position to a controller;

operating the controller to display the X-ray image in a proper orientation on a display by processing the image data and detected imaging position;

operating the controller to identify features of the dental structure of the patient from the image data and to display the X-ray image in a proper orientation on the display by processing the image data, detected imaging position, and identified features of the dental structure;

wherein the features of the dental structure comprise a root portion of a tooth in the dental structure; and operating the controller to compare the root portion to the gravitational vector to identify whether the image data relates to an upper or lower tooth in the mouth of the patient.

3. A method for applying radiation from an X-ray source to a dental structure in a mouth of a patient and then displaying an X-ray image of the dental structure in a correct orientation, the method comprising the steps of:

providing an intraoral sensor having a housing including a leading edge, a trailing edge, and a front surface for detecting radiation from the X-ray source;

providing an orientation sensor attached to the housing of the intraoral sensor;

providing a controller coupled to the intraoral sensor via a communication cable that extends outwardly beyond the trailing edge of the intraoral sensor, the controller configured to process image data from the intraoral sensor and orientation information from the orientation sensor;

inserting the leading edge of the intraoral sensor into the mouth of the patient followed by the trailing edge of the intraoral sensor so that the intraoral sensor is positioned in the mouth in one of at least two complementary imaging positions, including an imaging position on the left side of the dental structure wherein the front surface faces teeth on the left side of the dental structure and an imaging position on the right side of the dental structure wherein the front surface faces teeth on the right side of the dental structure, in one of which imaging positions the orientation sensor is inverted and thus has an orientation to the force of gravity that is the opposite of its orientation to the force of gravity in the other imaging position, and wherein the communication cable extends out of the mouth in each of the at least two complementary imaging positions;

applying radiation at a moment of imaging to the dental structure of the patient and the front surface of the intraoral sensor;

detecting radiation on the front surface of the intraoral sensor at the moment of imaging;

providing intraoral X-ray image data based on the detected radiation to the controller via the communication cable;

sensing the orientation of the orientation sensor by determining whether the orientation sensor has the same or opposite orientation with respect to the force of gravity at the moment of imaging;

providing the sensed orientation of the orientation sensor to the controller via the communication cable; and operating the controller to display an X-ray image in the correct orientation on a display based upon the sensed orientation of the orientation sensor and a known correlation between the orientation of the orientation sensor and the imaging positions on the left side of the dental structure and the right side of the dental structure.

4. The method according to claim 3, wherein if the orientation sensor is up side down with respect to gravity, the controller identifies the intraoral sensor to be in the imaging position on the left side of the dental structure and wherein if the orientation sensor is right side up with respect to gravity, the controller identifies the intraoral sensor to be in the imaging position on the right side of the dental structure.

* * * * *